(12) United States Patent
Hoshino et al.

(10) Patent No.: US 7,910,777 B2
(45) Date of Patent: Mar. 22, 2011

(54) METHOD FOR PRODUCING CYCLOALKANOL AND/OR CYCLOALKANONE

(75) Inventors: Masahiro Hoshino, Niihama (JP); Keisuke Sugita, Niihama (JP); Avelino Corma, Valencia (ES)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 12/560,788

(22) Filed: Sep. 16, 2009

(65) Prior Publication Data

US 2010/0069677 A1   Mar. 18, 2010

(30) Foreign Application Priority Data

Sep. 17, 2008 (JP) ................................ 2008-238225
Dec. 15, 2008 (JP) ................................ 2008-318118

(51) Int. Cl.
*C07C 45/32* (2006.01)
*C07C 35/18* (2006.01)
(52) U.S. Cl. ...................................... 568/357; 568/822
(58) Field of Classification Search .................. 568/357, 568/822
See application file for complete search history.

(56) References Cited

U.S. PATENT DOCUMENTS 7,692,044 B2 * 4/2010 Hoshino et al. ............... 568/357

FOREIGN PATENT DOCUMENTS

| EP | 1970364 A2 | 9/2008 |
|---|---|---|
| EP | 2030962 A1 | 3/2009 |
| EP | 1970364 A3 | 8/2009 |
| WO | 9216487 A1 | 10/1992 |

OTHER PUBLICATIONS

Kake Zhu et al., "Aerobic oxidation of cyclohexane by gold nanoparticles immobilized upon mesoporous silica", Catalysis Letters, vol. 100, Nos. 3-4, pp. 195-199, (2005).
Chen H. et al., "Synthesis, characterization and catalytic activities of mu-oxo-bridged binuclear iron complexes encapsulated in SBA-15", Journal Of Catalysis, vol. 257, No. 1, pp. 215-220, (2008).
Yasuhiko Kurusu et al., "Functionalization of Silica Gel: Application for the Catalytic Oxidation of Alkanes", Journal of Organic Chemistry, vol. 56, No. 6, pp. 1981-1983, (1991).
Maschmeyer T. et al., "Designing A Solid Catalyst for the Selective Low-Temperature Oxidation of Cyclohexane to Cyclohexanone", Angew. Chem. Int. Ed. Engl., vol. 36, No. 15, pp. 1639-1642, (1997).
Chen C. et al., "Catalytic Activity of Co-HMS Modified by Organic Groups for Cyclohexane Oxidation", Chinese Journal of Catalysis, vol. 29, No. 1, pp. 4-6, (2008).
Shylesh S. et al., "Heterogenized vanadyl cations over modified silica surfaces: A comprehensive understanding toward the structural property and catalytic activity difference over mesoporous and amorphous silica supports", Journal of Catalysis, vol. 244, No. 1, pp. 52-64, (2006).
Carvalho, Wagner Alves et al., "Iron and copper immobilized on mesoporous MCM-41 molecular sieves as catalysts for the oxidation of cyclohexane", Journal Of Molecular Catalysis A: Chemical 144 vol. 1, pp. 91-99, (1999).
Shylesh et al., "Chromium-containing small pore mesoporous silicas: Synthesis, characterization and catalytic behavior in the liquid phase oxidation of cyclohexane", Applied Catalysis A: General, vol. 318, pp. 128-136, (2007).
Tatsumi T. et al., "Remarkable activity enhancement by trimethylsilylation in oxidation of alkenes and alkanes with H2O2 catalyzed by titanium-containing mesoporous molecular sieves", Chemical Communications, pp. 325-326, (1998).
Jian-Zhou Gui et al., "Study on Au-Co/SBA-15 Catalyst for selective oxidation of cyclohexane" Applied Chemical Industry, vol. 35, No. 3, pp. 161-164, (2006).
Jian-Zhou Gui et al., "Synthesis and catalytic properties of Au-SBA-15 mesoporous zeolite", Industrial Catalysis, vol. 14, No. 5, pp. 56-60, (2006).
Shayong Liu et al., "Liquid-Phase Oxidation of Cyclohexane Using Co-P-MCM-41 CATALYST", Korean J. Chem. Eng., vol. 15, No. 5, pp. 510-515, (1998).

* cited by examiner

*Primary Examiner* — Sikarl A Witherspoon
(74) *Attorney, Agent, or Firm* — Panitch Schwarze Belisario & Nadel LLP

(57) ABSTRACT

The present invention provides a method for producing cycloalkanol and/or cycloalkanone,
which comprises reacting cycloalkane with molecular oxygen in the presence of mesoporous silica,
(1) the mesoporous silica containing at least one transition metal;
(2) the mesoporous silica having such pore distribution that the ratio of a total pore volume of mesoporous silica particles having a pore size of 3 to 50 nm to a total pore volume of mesoporous silica particles having a pore size of 2 to 50 nm is 50% or more; and
(3) the mesoporous silica being modified by an organic silicon compound.

5 Claims, No Drawings

METHOD FOR PRODUCING CYCLOALKANOL AND/OR CYCLOALKANONE

FIELD OF THE INVENTION

The present invention relates to a method for producing cycloalkanol and/or cycloalkanone by oxidizing cycloalkane with oxygen.

BACKGROUND OF THE INVENTION

Methods for producing cycloalkanol and/or cycloalkanone by cycloalkane oxidation with oxygen in the presence of mesoporous silica containing gold and/or cobalt has been known (Yingyong Huagong, Applied Chemical Industry, China, 2006, Vol. 35, p. 161-163, Gongye Cuihua, INDUSTRIAL CATALYSIS, China, 2006, Vol. 14, p. 56-60, and Korean Journal of Chemical Engineering, Korea, 1998, Vol. 15, p. 510-515).

The above described conventional methods, however, were not necessarily sufficient for their conversion rate of cycloalkane or selectivity to cycloalkanol and/or cycloalkanone.

According to the present invention, cycloalkanol and/or cycloalkanone can be produced with good conversion or selectivity.

The present invention relates to a method for producing cycloalkanol and/or cycloalkanone, which comprises reacting cycloalkane with molecular oxygen in the presence of mesoporous silica, (1) the mesoporous silica containing at least one transition metal;

(2) the mesoporous silica having such pore distribution that the ratio of a total pore volume of mesoporous silica particles having a pore size of 3 to 50 nm to a total pore volume of mesoporous silica particles having a pore size of 2 to 50 nm is 50% or more; and (3) the mesoporous silica being modified by an organic silicon compound (hereinafter referred to as "the present method").

The present invention will be described in detail below.

The cycloalkane in this specification means saturated cyclic hydrocarbon with or without side chain(s).

The cycloalkane include, monocyclic cycloalkanes without a side chain on their rings, such as cyclopropane, cyclobutane, cyclopentane, cyclohexane, cycloheptane, cyclooctane, cyclodecane, and cyclooctadecane, and polycyclic cycloalkanes, such as decalin and adamantane, and cycloalkanes with side chain(s) on their rings, such as methylcyclopentane and methylcyclohexane. Two or more of the cycloalkanes may be used together in the present method.

An oxygen-containing gas is generally used as the source of molecular oxygen. This oxygen-containing gas may be, for example, air, pure oxygen, or those diluted with an inert gas such as nitrogen, argon or helium. Oxygen-enriched air obtained by adding pure oxygen to air can also be used.

Examples of the transition metal include, for example, vanadium, chromium, manganese, iron, cobalt, ruthenium, and palladium. In particular, cobalt is preferable. Two or more transition metals may be used together, if necessary. The content of the transition metal in the mesoporous silica is generally 0.01 to 20 wt %, preferably 0.05 to 10 wt %, and more preferably 0.1 to 5 wt %. The metal may be incorporated into a silica framework constituting the mesoporous structure, or it may be incorporated into the pores of the mesoporous silica, or it may be supported on the silica framework surface.

The mesoporous silica having a pore distribution with the ratio of a total pore volume of mesoporous silica particles having a pore size of 3 to 50 nm to a total pore volume of mesoporous silica particles having a pore size of 2 to 50 nm being 50% or more is usually used in the present method, and the ratio is preferably 70% or more, and more preferably 85% or more.

The pore distribution of the mesoporous silica can be known by measuring a pore size and a pore volume according to the Barrett-Joyner-Halenda (BJH) analysis of an adsorption isotherm by a volumetric method at a liquid nitrogen temperature (77 K). Then, the ratio of a total pore volume of mesoporous silica particles having a pore size of 3 to 50 nm to a total pore volume of mesoporous silica particles having a pore size of 2 to 50 nm can be calculated from pore distribution found by the measurements.

The specific surface area of the mesoporous silica used in the present invention is generally about 600 to 1500 m²/g.

The mesoporous silica used in the present method is a mesoporous silica containing at least one transition metal and having the specific pore distribution as described above and is modified by an organic silicon compound. Modification with the organic silicon compound is typically conducted by contacting a silicon compound capable of bonding to the surface of the mesoporous silica when contacted. Typical examples of the organic silicon compound include a silicon compound of formula (I):

$$Si(R^1)_x(R^2)_{4-x} \qquad (I)$$

wherein $R^1$ represents an alkoxy group, a hydroxyl group, a halogen atom, or a trialkylsilylamino group, $R^2$ represents an alkoxy group, an alkyl group, an allyl group, an aryl group, or an aralkyl group, and x represents an integer of 1 to 3.

As the organic silicon compound particularly preferred is, trialkoxyalkylsilane or tetraalkoxysilane. The contact treatment is typically conducted by a method of immersing the crystal (silica having a mesoporous structure) after calcination in a liquid containing an organic silicon compound, or by a method of bringing a crystal (silica having a mesoporous structure) after calcination into contact with a gas containing the organic silicon compound.

The amount of the organic silicon compound that may be used is generally 1 to 10000 parts by weight, preferably 5 to 2000 parts by weight, and more preferably 10 to 1500 parts by weight per 100 parts by weight of the silica before the contact treatment with the organic silicon compound.

A temperature for the contact treatment with an organic silicon compound is generally 0 to 300° C., and preferably 30 to 250° C. A time for the contact treatment is generally 0.1 to 50 hours, and preferably 1 to 20 hours.

The mesoporous silica containing at least one transition metal and having the specific pore distribution is typically prepared by 1) performing a hydrothermal synthesis reaction with a mixture containing tetraalkoxysilane, a predetermined structure-directing agent, and water (said mixture is referred to as "mixture for hydrothermal reaction") to obtain a crystal (silica having a mesoporous structure), 2) calcining the crystal to obtain mesoporous silica, and 3) contacting the calcined crystal with at least one transition metal compound.

Alternatively, the mesoporous silica containing at least one transition metal and having the specific pore distribution is prepared as follows. For example, the transition metal compound, such as halide, nitrate, carboxylate, and oxoate (oxyacid salt) of the transition metals, is mixed with tetraalkoxysilane, a predetermined structure-directing agent and water, and the resulting mixture is subjected to a hydrothermal synthesis reaction to obtain a mesoporous silica crystal containing the transition metal compound.

The predetermined structure-directing agent is suitably selected. For preparing SAB-3 type mesoporous silica a gemini surfactant (e.g., $C_nH_{2n+1}(CH_3)_2N^+(CH_2)_sN^+(CH_3)_2C_mH_{2m+1}$, wherein n s, and m each represent an integer of 1 or more) is selected as a structure-directing agent as described in Catalysis Communications, Holland, 2008, Vol. 9, No. 13, p. 2287-2290.

For HMS type mesoporous silica, long chain alkylamine ($C_nH_{2n+1}NH_2$, wherein n represents a integer of 1 or more) is selected as a structure-directing agent as described in Applied Catalysis A: General, Holland, 2008, Vol. 347, p. 133-141.

For MSU-X type mesoporous silica, oleyl decaoxyethylene is selected as a structure-directing agent as described in Microporous and Mesoporous Materials, Holland, 2008, Vol. 109, p. 199-209.

For SBA-12 type mesoporous silica, polyethylene oxide is selected as a structure-directing agent as described in Journal of Physical Chemistry B, USA, 2002, Vol. 106, p. 3118-3123.

For SBA-15 type mesoporous silica, a triblock copolymer (polyethylene oxide-polypropylene oxide-polyethylene oxide copolymer) is selected as a structure-directing agent as described in Science, USA, Vol. 279, p. 548-552, and Microporous and Mesoporous Materials, Holland, 2006, Vol. 91, p. 156.

For preparing SBA-16 type mesoporous silica, a triblock copolymer (polyethylene oxide-polypropylene oxide-polyethylene oxide copolymer) is selected as a structure-directing agent as described in Microporous and Mesoporous Materials, Holland, 2007, Vol. 105, p. 15-23.

Among these, SBA-12 type, SBA-15 type, and SBA-16 type mesoporous silica are preferable, and SBA-15 type is more preferable. Among the above structure-directing agents, in particular, polyalkylene oxide such as polyethylene oxide and a triblock copolymer (polyethylene oxide-polypropylene oxide-polyethylene oxide copolymer) are preferable. A molecular weight of the polyalkylene oxide referred herein is usually about 500 to 15000. The triblock copolymer usually used herein has a polymerization unit ratio by weight of polyethylene oxide:polypropylene oxide:polyethylene oxide about 5:70:5 to 110:70:110.

The structure-directing agent is generally used in an amount of 0.1 to 1 mol, and preferably 0.2 to 0.5 mol per mol of the tetraalkoxysilane. The amount of water is generally 5 to 30 parts by weight, and preferably 10 to 15 parts by weight per part by weight of the tetraalkoxysilane. In addition, acids, for example, inorganic acids such as hydrochloric acid (aqueous solution of hydrogen chloride) and sulfuric acid, and organic acids such as acetic acid and citric acid, and bases such as sodium hydroxide and potassium hydroxide may be added to the mixture, if necessary, to perform a hydrothermal synthesis reaction.

The reaction temperature of the hydrothermal reaction is generally 20 to 200° C., and preferably 20 to 150° C. The reaction time is generally 0.1 to 400 hours, and preferably 1 to 200 hours.

The contact of the calcined crystal (mesoporous silica) with at least one transition metal compound is conducted by impregnation, in which the crystal (mesoporous silica) is immersed in the solution of the transition metal compound to adsorbed the transition metal, or the crystal is subjected to ionic exchange with a cation of the crystal.

Calcination temperature is generally about 500 to 600° C., and calcination time is generally 1 to 20 hours.

The mesoporous silica thus obtained is then treated by contacting with the organic silicon compound. Desired mesoporous silica can be thus obtained. Then, cycloalkane is oxidized with molecular oxygen in the presence of this mesoporous silica. The mesoporous silica is generally used in an amount of 0.01 to 50 parts by weight, and preferably 0.1 to 10 parts by weight per 100 parts by weight of the cycloalkane.

A reaction temperature for oxidizing cycloalkane is generally 0 to 200° C., and preferably 50 to 170° C., and a reaction pressure is generally 0.01 to 10 MPa, and preferably 0.1 to 2 MPa. A reaction solvent can be used, if necessary, and for example, nitrile solvents such as acetonitrile and benzonitrile, carboxylic acid solvents such as acetic acid and propionic acid, and the like can be used.

Post-treatment operations after the oxidation reaction are not limited, and examples thereof include such as a method in which a reaction mixture is filtered to separate a catalyst, then washed with water, and subsequently distilled to obtain a reaction mixture.

Cycloalkyl hydroperoxide resulting from cycloalkane that may be contained in the reaction mixture can be converted into desired cycloalkanol or cycloalkanone, for example, by an alkali treatment, reduction treatment or the like.

EXAMPLES

Examples of the present invention will be shown in the following, but the present invention is not limited by these examples. Analyses of cyclohexane, cyclohexanone, cyclohexanol, and cyclohexyl hydroperoxide in a reaction solution were performed by gas chromatography, and from the analysis results, the conversion rate of cyclohexane, and respective selectivities to cyclohexanone, cyclohexanol, and cyclohexyl hydroperoxide were calculated.

In these examples, a pore distribution of mesoporous silica was determined from a BJH analysis of an adsorption isotherm by a volumetric method at a liquid nitrogen temperature (77 K). The measurement method thereof is as follows.

A glass test tube (volume of 4 ml, tube inner diameter of 6 mm) was set in BELPREP-vacII manufactured by BEL Japan, Inc. and evacuated the tube of air, and tared, subsequently about 0.05 g of a powdery test sample was filled in the test tube, and the test tube in BELPREP-vacII was again pretreated in vacuum at 150° C. for 3 hours, thereafter weighing the test tube again and subtracting the tare weight to determine a real powdery sample amount. Then, the test tube after the vacuum pretreatment was set in BELPREP-mini manufactured by BEL Japan, Inc., and an inherent volume to each test tube (dead volume) was measured and subsequently a saturated vapor pressure of nitrogen was measured, thereafter measuring an adsorption equilibrium pressure. These operations were repeated until a relative pressure that is a ratio of the adsorption equilibrium pressure to the initial pressure was 0.99 to obtain an absorption isotherm. A pore distribution was found by calculating a pore size and a pore volume based on the Barrett-Joyner-Halenda (BJH) theory utilizing capillary condensation of nitrogen gas on the assumption of a cylindrical pore.

Production Example 1

Production of SBA-15 Type Mesoporous Silica

SBA-15 type mesoporous silica was synthesized as follows using a triblock copolymer (Pluronic P123) as a structure-directing agent based on the method described in Science, USA, Vol. 279, p. 548-552. 4 g of Pluronic P123 (made by Sigma-Aldrich Corporation) was added to 30 g of water to be dispersed and, while stirring the dispersion, thereto were then added 120 g of 7 wt %-hydrochloric acid (an aqueous hydrogen chloride solution), 0.3 g of cobalt nitrate and 0.9 g of citric acid. Then, 8.5 g of tetraethoxysilane (ethyl orthosilicate, made by Wako Pure Chemical Industries, Ltd.) was added and stirred at 60° C. for 41 hours, and then, the mixture was subjected to hydrothermal synthesis at 100° C. for 2 days. The obtained mixture was filtered and collected residue was washed with water and then dried at 60° C. overnight. The obtained dried product was calcined at 500° C. for 7 hours under air flow. When an analysis according to the above method was carried out on the powder obtained by calcination (SBA-15 type mesoporous silica), the ratio of a total pore volume of mesoporous silica particles having a pore size of 3 to 50 nm to a total pore volume of mesoporous silica particles having a pore size of 2 to 50 nm was 85%.

Production Example 2

Cobalt-Supporting SBA-15 Type Mesoporous Silica 0.2 g of the powder obtained in Production Example 1, 25.2 g of water, 1.11 g of 7.5 wt %-ammonium nitrate aqueous solution, 1.7 g of 25 wt %-ammonia water, and 0.042 g of cobalt acetate tetrahydrate were mixed and stirred at room temperature for 2 hours. The obtained mixture was filtered, and the filtration residue was washed with water and then dried at 110° C. for 12 hours to thus obtain SBA-15 type mesoporous silica containing cobalt.

Production Example 3

Contact Treatment with Trimethoxypropylsilane on SSA-15 Type Mesoporous Silica Containing Cobalt A eggplant-shaped flask was charged with 0.2 g of the SBA-15 type mesoporous silica containing cobalt, obtained in Production Example 2, and 2.0 g of trimethoxypropylsilane (made by TOKYO CHEMICAL INDUSTRY CO., LTD.), and the resulting mixture was stirred at 90° C. for 7.5 hours under a nitrogen atmosphere. After the obtained mixture was cooled to room temperature, ethanol was added thereto and the resulting mixture was stirred and then filtered. The collected residue was washed with ethanol and then dried at room temperature overnight to obtain a contact-treated product of SBA-15 type mesoporous silica containing cobalt with trimethoxypropylsilane (hereinafter referred to as mesoporous silica A).

Production Example 4

Production of MCM-41 Type Mesoporous Silica Containing Cobalt

MCM-41 type mesoporous silica containing cobalt was synthesized as follows, using hexadecyl trimethyl ammonium bromide as a structure-directing agent based on the method described in Applied Catalysis A: General, Holland, 2004, Vol. 272, p. 257-266. A 1 L-beaker was charged with 17.6 g of hexadecyl trimethyl ammonium bromide (made by Wako Pure Chemical Industries, Ltd.), 327.1 g of water, 106.9 g of ethanol (made by Wako Pure Chemical Industries, Ltd.), 33.8 g of tetraethoxysilane (ethyl orthosilicate, made by Wako Pure Chemical Industries, Ltd.), 119.3 g of 25 wt %-ammonia water (made by Wake Pure Chemical Industries, Ltd.), and 0.042 g of cobalt acetate (II) tetrahydrate (made by Wako Pure Chemical Industries, Ltd.), and the mixture was stirred at room temperature for 2 hours and filtered, and the collected residue was washed with water and then dried at 100° C. for 12 hours. Then, the dried product was calcined at 550° C. for 7 hours under air flow. When an analysis according to the above method was carried out with the powder obtained by calcining (MCM-41 type mesoporous silica containing cobalt), the ratio of a total pore volume of mesoporous silica particles having a pore size of 3 to 50 nm to a total pore volume of mesoporous silica particles having a pore size of 2 to 50 nm was 11%.

Production Example 5

Contact Treatment with Trimethoxypropylsilane on MCM-41 Type Mesoporous Silica Containing Cobalt A flask was charged with 0.3 g of the MCM-41 type mesoporous silica containing cobalt obtained in Production Example 4 and 3.0 g of trimethoxypropylsilane (made by TOKYO CHEMICAL INDUSTRY CO., LTD.), and the resulting mixture was stirred at 90° C. for 7.5 hours under a nitrogen atmosphere. After the obtained mixture was cooled to room temperature, ethanol was added thereto and the mixture was stirred and then filtered. Collected residue was washed with ethanol and then dried at room temperature overnight to obtain a trimethoxypropylsilane-treated product of MCM-41 type mesoporous silica containing cobalt (hereinafter referred to as mesoporous silica B).

Example 1

300 g of cyclohexane (3.6 mol) and 0.2 g of the mesoporous silica A obtained in Production Example 3 were placed in a 1 L-autoclave, a pressure inside the system was increased to 0.70 MPa with nitrogen at room temperature and the temperature was then raised to 140° C., and subsequently, air was supplied at 200 ml/min to perform a reaction for 3.5 hours.

At the time of 1.5 hours from initiation of the reaction, the conversion rate of cyclohexane was 4.2%, the selectivity to cyclohexanone was 35.3%, the selectivity to cyclohexanol was 48.6%, the selectivity to cyclohexyl hydroperoxide was 7.2% (total selectivity: 91.1%). At the time of 2.5 hours from initiation of the reaction, the conversion rate of cyclohexane was 6.9%, the selectivity to cyclohexanone was 38.5%, the selectivity to cyclohexanol was 45.5%, the selectivity to cyclohexyl hydroperoxide was 5.1% (total selectivity: 89.1%). At the time of 3.5 hours (at the time of completion) from initiation of the reaction, the conversion rate of cyclohexane was 9.4%, the selectivity to cyclohexanone was 41.3%, the selectivity to cyclohexanol was 42.3%, the selectivity to cyclohexyl hydroperoxide was 3.5% (total selectivity: 87.1%).

Comparative Example 1

The same operations as in Example 1 were performed except that the SBA-15 type mesoporous silica containing cobalt obtained in Production Example 2 (contact treatment with an organic silicon compound was not performed) was used in place of the mesoporous silica A obtained in Production Example 3.

At the time of 1.5 hours from initiation of the reaction, the conversion rate of cyclohexane was 3.7%, the selectivity to cyclohexanone was 31.3%, the selectivity to cyclohexanol was 51.1%, the selectivity to cyclohexyl hydroperoxide was 6.3% (total selectivity: 88.7%). At the time of 2.5 hours from initiation of the reaction, the conversion rate of cyclohexane was 6.5%, the selectivity to cyclohexanone was 36.0%, the selectivity to cyclohexanol was 46.3%, the selectivity to cyclohexyl hydroperoxide was 5.1% (total selectivity: 87.4%). At the time of 3.5 hours (at the time of completion) from initiation of the reaction, the conversion rate of cyclohexane was 8.8%, the selectivity to cyclohexanone was 40.1%, the selectivity to cyclohexanol was 42.8%, the selectivity to cyclohexyl hydroperoxide was 3.3% (total selectivity: 86.2%).

Comparative Example 2

The same operations as in Example 1 were performed except that the mesoporous silica B obtained in Production Example 5 was used in place of the mesoporous silica A obtained in Production Example 3.

At the time of 1.5 hours from initiation of the reaction, the conversion rate of cyclohexane was 4.2%, the selectivity to cyclohexanone was 30.4%, the selectivity to cyclohexanol was 53.3%, the selectivity to cyclohexyl hydroperoxide was 4.8% (total selectivity 88.5%). At the time of 2.5 hours from initiation of the reaction, the conversion rate of cyclohexane was 7.0%, the selectivity to cyclohexanone was 36.0%, the selectivity to cyclohexanol was 47.6%, the selectivity to cyclohexyl hydroperoxide was 2.9% (total selectivity: 86.5%). At the time of 3.5 hours (at the time of completion) from initiation of the reaction, the conversion rate of cyclohexane was 9.6%, the selectivity to cyclohexanone was 40.2%, the selectivity to cyclohexanol was 42.0%, the selectivity to cyclohexyl hydroperoxide was 2.2% (total selectivity: 84.4%).

What is claimed is:

1. A method for producing cycloalkanol and/or cycloalkanone, which comprises reacting cycloalkane with molecular oxygen in the presence of mesoporous silica, (1) the mesoporous silica containing at least one transition metal selected from the group consisting of vanadium, chromium, manganese, cobalt, ruthenium, and palladium;
   (2) the mesoporous silica having pore distribution with the ratio of a total pore volume of mesoporous silica particles having a pore size of 3 to 50 nm to a total pore volume of mesoporous silica particles having a pore size of 2 to 50 nm being 50% or more; and
   (3) the mesoporous silica being modified by an organic silicon compound, and wherein the mesoporous silica is obtained by the steps of
   performing a hydrothermal synthesis reaction with a mixture containing tetraalkoxysilane, polyalkylene oxide and water to obtain a mesoporous silica,
   calcining the mesoporous silica,
   bringing the mesoporous silica in contact with a transition metal compound to produce a mesoporous silica-containing transition metal, and then
   treating the resulting mesoporous silica with an organic silicon compound of formula (I):

$$Si(R^1)_x(R^2)_{4-x} \quad (I)$$

wherein $R^1$ represents an alkoxy group, a hydroxyl group, a halogen atom, or a trialkylsilylamino group, $R^2$ represents an alkoxy group, an alkyl group, an allyl group, an aryl group, or an aralkyl group, and x represents an integer of 1 to 3.

2. The production method according to claim 1, wherein the mesoporous silica is at least one mesoporous silica selected from the group consisting of SBA-12 type, SBA-15 type, and SBA-16 type.

3. The production method according to claim 1, wherein the transition metal is cobalt.

4. The production method according to claim 1, wherein the organic silicon compound is trialkoxyalkylsilane or tetraalkoxysilane.

5. The production method according to claim 1, wherein cycloalkane is cyclohexane.

* * * * *